(12) United States Patent
Wu et al.

(10) Patent No.: US 8,449,924 B2
(45) Date of Patent: *May 28, 2013

(54) PROCESS FOR THE PREPARATION OF PLANT EXTRACTS FOR TREATING SKIN DISORDERS AND ENHANCING HEALING OF WOUNDS

(75) Inventors: Rey-Yuh Wu, Taipei (TW); Yuh-Shan Chung, Taipei (TW); Yu-Yuan Wu, Taipei (TW); Ma-Li Siu, Taipei (TW); Chin-Wen Hsiao, Taipei (TW)

(73) Assignee: Development Center for Biotechnology, Taipei County (TW)

( * ) Notice: Subject to any disclaimer, the term of this patent is extended or adjusted under 35 U.S.C. 154(b) by 995 days.

This patent is subject to a terminal disclaimer.

(21) Appl. No.: 11/847,220

(22) Filed: Aug. 29, 2007

(65) Prior Publication Data

US 2009/0060985 A1    Mar. 5, 2009

(51) Int. Cl.
*A61K 36/00*    (2006.01)

(52) U.S. Cl.
USPC ........................................................ 424/725

(58) Field of Classification Search
None
See application file for complete search history.

(56) References Cited

U.S. PATENT DOCUMENTS

| 4,318,906 | A | 3/1982 | Llopart |
| 5,834,437 | A | 11/1998 | Jew et al. |
| 6,267,996 | B1 | 7/2001 | Bombardelli et al. |
| 6,417,349 | B1 | 7/2002 | Kim et al. |
| 6,475,536 | B2 | 11/2002 | Bombardelli et al. |
| 2006/0099283 | A1 | 5/2006 | Wei et al. |

FOREIGN PATENT DOCUMENTS

| CN | 1313124 A | 7/1994 |
| CN | 1194154 A | 9/1998 |
| CN | 1089497 A | 9/2001 |
| CN | 1137681 C | 6/2002 |
| JP | 09078062 A | * 3/1997 |
| JP | 2004059482 A | * 2/2004 |

OTHER PUBLICATIONS

Lukhoba et al. Plectranthus: A review of ethnobotanical uses. Journal of Ethanopharmacology. vol. 103, Issue 1 (Jan. 3, 2006) 1-24.*
Extended European Search Report, Jan. 5, 2009, EP1925310.
Abstract of Revista da Sociedade Brasileira de Medicina Tropical, vol. 29 No. 3, May 1996, pp. 229-232.
Phytomedicine, vol. 8, No. 5, Jan. 1, 2001, pp. 395-400.
Journal of Ethnopharmacology, vol. 103, No. 1, Jan. 3, 2006, pp. 1-24.
Indian Journal of Pharmacology, vol. 37, No. 1, Feb. 2005, pp. 37-45.
*Aspergillus nidulans*. Journal of Ethnopharmacology, vol. 52, 1996, pp. 123-127.
Angiology, vol. 52, No. 2, Oct. 1, 2001, pp. S27-S31.
Angiology, vol. 52, No. 2, Oct. 1, 2001, pp. S49-S54.

* cited by examiner

*Primary Examiner* — Amy L Clark
(74) *Attorney, Agent, or Firm* — WPAT, P.C.; Anthony King

(57) ABSTRACT

The present invention provides a process for the preparation of *Plectranthus amboinicus* extracts using a stirring separation method. The present invention also relates to a pharmaceutical composition comprising the *Plectranthus amboinicus* crude extract and/or extract for treating skin disorders, including enhancing the healing of wounds, especially in diabetic patients.

6 Claims, 3 Drawing Sheets

PROCESS FOR THE PREPARATION OF PLANT EXTRACTS FOR TREATING SKIN DISORDERS AND ENHANCING HEALING OF WOUNDS

FIELD OF THE INVENTION

The present invention relates to a process for the preparation of Chinese herbal medicine extracts. Specifically, the present invention relates to the use of a solid-liquid separation in combination with a specific treatment for mass production of a plant extract for treating skin disorders, including enhancing the healing of wounds, especially in diabetic patients.

BACKGROUND OF THE INVENTION

*Plectranthus amboinicus* (Lour.) Spreng, growing in Malaysia and India, is a decorative medicinal herb commonly cultivated by ordinary families. The medicinal part of *Plectranthus amboinicus* is the epigeal portion. *Plectranthus amboinicus* is also known as Cuban oregano, Indian borage, Indian mint, Mexican mint, Mexican oregano or Spanish thyme. East Indians use *Plectranthus amboinicus* as a fabric aromatic, and the English discovered its attractive fragrance when importing shawl fabrics from India in the 1820's. When the *Plectranthus amboinicus* leaves are put directly with clothing, it not only has an aromatic effect, but also prevents the clothing from being eaten by moths. It is thought to be useful for disinfection, enhancing sexual excitement and preventing insect bites. In addition, *Plectranthus amboinicus* may be used for treating poisonous snake bites and relieving symptoms such as headache, flatulence, vomiting, diarrhea and fever. Moreover, *Plectranthus amboinicus* oil is a popular perfume in Asia, and it is used in aromatherapy for improving epithelia regeneration, treating acne, and relieving the symptoms of eczema, Athlete's foot and dry cracked skin. Furthermore, *Plectranthus amboinicus* is a good tranquilizer and aphrodisiac that can relieve anxiety and enhance sexual desire.

Various uses of *Plectranthus amboinicus* are reported in general magazines, but scientific studies on *Plectranthus amboinicus* are rarely seen in literature. US 2006/0099283 A1 discloses leaf juice of *Plectranthus amboinicus* for treating cancer and/or tumor. U.S. Ser. No. 11/605,178, a patent application relating to the present invention, provides a pharmaceutical composition comprising a therapeutically effective amount of *Plectranthus amboinicus* crude extracts/extracts and a therapeutically effective amount of *Centella asiatica* Urban extracts.

*Centella asiatica* Urban (pennywort) is a plant naturally growing in the coastal areas of Madagascar and the Indian Ocean. The medicinal part of *Centella asiatica* Urban of the Apiaceae family is its dried whole plant. *Centella asiatica* Urban is also known as European water-marvel, Gotu kola, Kola, Indian pennywort, Indian ginseng, Horse-hoof grass, Pegaga, Mandookaparni, Tiger herbal, Spadeleaf, or Tono. For hundreds of years, *Centella asiatica* Urban has been thought to be useful in the traditional medicine of Asia for improving wound healing. The extracts of *Centella asiatica* Urban comprise two major compounds: asiaticoside and madecassic acid. *Centella asiatica* Urban extracts are used to treat burns and trauma and prevent postoperative adhesion, and the preparation methods of *Centella asiatica* Urban extracts have been described in some patent applications. For example, U.S. Pat. No. 4,318,906 and CN 1353972A disclose the medical uses of *Centella asiatica* Urban as the single active ingredient; U.S. Pat. Nos. 6,475,536, 6,267,996, CN 1313124A, CN 93110425.4 and CN 1089497A disclose the use of *Centella asiatica* Urban in combination with other substances for cosmetic formulation, treating burns or making ointment for trauma; and U.S. Pat. Nos. 5,834,437, 6,417, 349 and CN 1194154A disclose the methods for preparing *Centella asiatica* Urban extracts.

Conventional separation processes for separating the components from the mixture include contacting the mixture with a nonionic absorbing resin such as DIAION® HP20, DIAION® HP20SS, Sepabeads® SP207 (Mitsubishi Chemical Corporation), Amberlite™ XAD-2 (Rohm and Hass company), Amberlite™ XAD-4, and the like. The steps comprise packing the nonionic absorbing resin into a separation column, adding the mixture to the column, and eluting the column with a solvent. When such process is taken to treat a massive amount of a mixture, it is time-consuming and the elution conditions are not easily controlled.

The leaf juice of US 2006/0099283 A1 was obtained by grinding and removing tissue fragments and/or residues, and the different fractions of the leaf juice were separated with centrifugal filter devices.

The *Plectranthus amboinicus* extracts of U.S. Ser. No. 11/605,178 were prepared by utilizing a series of solvents with different polarities to elute the extracts from a chromatographic column. This method is complicated and time-consuming. There is still a need to provide a method for obtaining in large quantities the active ingredients of *Plectranthus amboinicus*.

Surprisingly, we found that a stirring method can replace the traditional column separation method and be used for mass production of *Plectranthus amboinicus* extracts. The stirring method is fast and the elution conditions can be easily controlled. Moreover, *Plectranthus amboinicus* extracts obtained by stirring separation are more effective than extracts prepared by column chromatographic separation.

SUMMARY OF THE INVENTION

One of the purposes of the present invention is to provide a process for preparing *Plectranthus amboinicus* crude extract and/or extracts.

Another purpose of the present invention is to provide a pharmaceutical composition for treating skin disorders (including enhancing the healing of wounds in diabetic patients), comprising a therapeutically effective amount of *Plectranthus amboinicus* crude extracts and/or extracts. The pharmaceutical composition may further comprise a therapeutically effective amount of *Centella asiatica* Urban extracts.

Still another purpose of the present invention is to provide a wound dressing comprising the pharmaceutical composition of this invention.

A further purpose of the present invention is to provide a method for treating skin disorder comprising administering the pharmaceutical composition of this invention.

The present invention is described in detail in the following sections. Other characterizations, purposes and advantages of the present invention can be easily found in the detailed descriptions and claims of the invention.

DETAILED DESCRIPTION OF THE INVENTION

Figure 1:
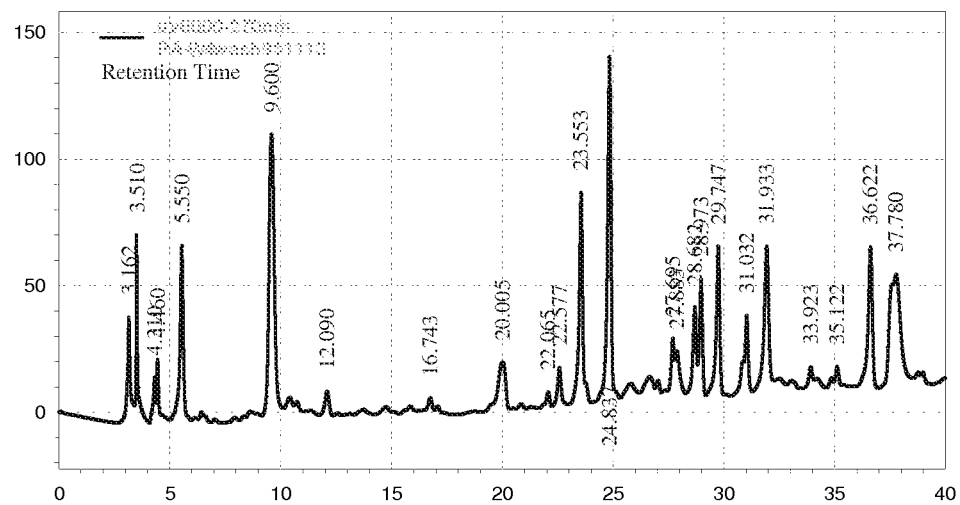
FIG. 1 shows the chromatographic spectrum of the *Plectranthus amboinicus* extract (PA-W4) prepared by stirring separation. The spectrum was determined by Reverse Phase HPLC at UV 270 nm.

Unless otherwise defined herein, scientific and technical terms used in connection with the present invention shall have the meanings that are commonly understood by those of ordinary skill in the art. The meaning and scope of the terms should be clear; however, in the event of any latent ambiguity, definitions provided herein take precedence over any dictionary or extrinsic definition.

As utilized in accordance with the present disclosure, the following terms, unless otherwise indicated, shall be understood to have the following meanings:

The term "skin disorders" as used herein includes wounds or sores. In one embodiment, skin disorders include cuts, lacerations, abrasions, stabs or other similar skin injuries, preferably a diabetic patient's wounds; sores include bedsores.

The term "treating" or "enhancing" as used herein denotes improving the symptoms.

The term "patients" as used herein denotes animals, especially mammals. In one preferred embodiment, the term "patients" denotes "humans."

The term "therapeutically effective amount" as used herein refers to the amount of the pharmaceutical composition used alone or in combination with other medicaments for treating disorders that shows therapeutic efficacy.

The term "carrier" or "pharmaceutically acceptable carrier" refers to diluents, excipients, acceptors or analogues, which are well known to persons of ordinary skill in the art for manufacturing pharmaceutical compositions.

The term "*Centella asiatica* Urban extracts" denotes extracts of dried *Centella asiatica* Urban whole plants, wherein the major active components comprise asiaticoside and madecassic acid. Preferably, it is the medicinal part available on the market that mainly comprises asiaticoside and madecassic acid, and its purity is greater than 70%.

The term "*Plectranthus amboinicus* crude extract" denotes an extract obtained from the epigeal portion of *Plectranthus amboinicus*, and the crude extract may be further concentrated.

The term "*Plectranthus amboinicus* extract" denotes an extract obtained from the crude extract by further separation(s).

The term "high-polarity solvent" denotes a solvent that has the highest polarity in the solvents used in the preparation process. The high-polarity solvent includes, but is not limited to, water, methanol, ethanol or a mixture of two or more of the preceding solvents.

The term "low-polarity solvent" denotes a solvent that has the lowest polarity in the solvents used in the preparation process. The low-polarity solvent includes, but is not limited to, chloroform, isopropanol, acetone, ethyl acetate, a mixture of two or more of the preceding solvents, or a mixture of one or more of the preceding solvents with one or more solvent that have higher polarity.

The term "sub-high-polarity solvent" denotes a solvent that has a polarity lower than that of the high-polarity solvent used in the preparation process but higher than that of the medium-polarity solvent used in the preparation process. The sub-high-polarity solvents can be obtained by mixing a high-polarity solvent with a solvent having lower polarity in a ratio (v:v) of about 30:70 to about 70:30, preferably of about 60:40 to about 40:60.

The term "medium-polarity solvent" denotes a solvent that has a polarity lower than that of the sub-high-polarity solvent used in the preparation process but higher than that of the low-polarity solvent used in the preparation process. The medium-polarity solvents can be obtained by mixing a high-polarity solvent with a solvent having lower polarity in a ratio (v:v) of about 30:70 to about 5:95, preferably of about 15:85 to about 5:95.

Unless otherwise required by context, singular terms shall include the plural and plural terms shall include the singular.

The Preparation Processes

The present invention is characterized by using solid-liquid separation (stirring separation) in combination with a specific treatment for mass production of *Plectranthus amboinicus* extracts in a faster manner with a higher yield. The stirring separation comprises stirring an absorbing resin, such as DIAION, into the *Plectranthus amboinicus* extract and separating the different fractions from the *Plectranthus amboinicus* extracts by differential separation steps with the utilization of different solvents. In addition to higher throughput, the *Plectranthus amboinicus* extract obtained by the process of the present invention is more effective than that prepared by the column chromatographic separation method.

The process of the present invention for preparing *Plectranthus amboinicus* extracts comprises the steps of:
  contacting the dried *Plectranthus amboinicus* leaves with a leaf extracting solvent to obtain a *Plectranthus amboinicus* crude extract;
  concentrating the *Plectranthus amboinicus* crude extract; and
  treating the concentrated *Plectranthus amboinicus* crude extract using a stirring separation method to obtain a *Plectranthus amboinicus* extract.

According to the present invention, the stirring separation method comprises the following steps:
  (a) diluting the concentrated *Plectranthus amboinicus* crude extract with a high-polarity solvent, mixing the diluted *Plectranthus amboinicus* crude extract with an absorbing resin, and stirring the absorbing resin and the diluted *Plectranthus amboinicus* crude extract;
  (b) removing the liquid portion, extracting the resin with distilled water, and collecting the first extract;
  (c) extracting the resin with a sub-high-polarity solvent and collecting the second extract;
  (d) extracting the resin with a medium-polarity solvent and collecting the third extract; and
  (e) extracting the resin with a low-polarity solvent and collecting the fourth extract.

In one preferred embodiment, the process for preparing *Plectranthus amboinicus* extracts comprises the steps of:
1. contacting dried *Plectranthus amboinicus* leaves with a leaf extracting solvent for about 30 to about 100 hours to obtain a *Plectranthus amboinicus* crude extract;
2. concentrating the *Plectranthus amboinicus* crude extract;
3. diluting the concentrated *Plectranthus amboinicus* crude extract with a high-polarity solvent and mixing the diluted *Plectranthus amboinicus* crude extract with an absorbing resin by stirring for about 10 to about 30 hours;
4. removing the liquid portion;
5. dipping the resin in distilled water for about 1 to about 7 hours to obtain a first extract (PA-W1);
6. mixing and stirring the resin with a sub-high-polarity solvent for about 1 to about 7 hours to obtain a second extract (PA-W2);
7. mixing and stirring the resin with a medium-polarity solvent for about 1 to about 7 hours to obtain a third extract (PA-W3);
8. mixing and stirring the resin with a low-polarity solvent for about 1 to about 7 hours to obtain a fourth extract (PA-W4).

According to the process of the present invention, the leaf extracting solvent is selected from, but not limited to, water and alcohols. In one preferred embodiment, the alcohol is ethanol. The ratio of the volume of the leaf extracting solvent to the weight of the dried *Plectranthus amboinicus* leaves is about 6:1 to about 15:1, preferably about 10:1.

According to the process of the present invention, the leaf extract obtained in step 1 may be concentrated by any conventional concentration methods for solutions, such as using a pressure-reducing rotary evaporator.

According to the process of the present invention, the absorbing resin is selected from, but not limited to, DIAION® HP20, DIAION® HP20SS, Sepabeads® SP207, Amberlite™ XAD-2, Amberlite™ XAD-4, and the like, preferably the DIAION® series. In one preferred embodiment, the absorbing resin is DIAION® HP20. In addition, the DIAION® HP20 resin can be pre-treated with methanol.

According the process of the present invention, the ratio of the volume of the high-polarity solvent to the weight of the dried *Plectranthus amboinicus* leaves is about 8:1 to about 4:1, preferably about 5:1; the ratio of the volume of the sub-high-polarity solvent to the weight of the dried *Plectranthus amboinicus* leaves is about 8:1 to about 4:1, preferably about 5:1; the ratio of the volume of the medium-polarity solvent to the weight of the dried *Plectranthus amboinicus* leaves is about 8:1 to about 4:1, preferably about 5:1; and the ratio of the volume of the low-polarity solvent to the weight of the dried *Plectranthus amboinicus* leaves is about 8:1 to about 4:1, preferably about 5:1.

According to the process of the present invention, the extraction period of step 1 is about 30 to about 100 hours, preferably 50 to about 80 hours, and most preferably more than about 72 hours. The absorption period of step 3 is about 10 to about 30 hours, preferably about 17 to about 25 hours, and most preferably more than about 20 hours. The extraction period of step 5 is about 1 to about 7 hours, preferably about 1 to about 4 hours, and most preferably about 1 hour. The extraction period of step 6 is about 1 to about 7 hours, preferably about 1 to about 4 hours, and most preferably about 1 hour. The extraction period of step 7 is about 1 to about 7 hours, preferably about 1 to about 4 hours, and most preferably about 1 hour. The extraction period of step 8 is about 1 to about 7 hours, preferably about 1 to about 4 hours, and most preferably about 1 hour.

Furthermore, according to the process of the present invention, stirring is conducted at the speed of about 3 to about 15 rpm, preferably about 5 to about 10 rpm, and most preferably 7 rpm.

The process of the present invention is a high-throughput method for mass production of *Plectranthus amboinicus* extracts. The process is about five times faster than the column chromatographic separation method to extract the active fractions from *Plectranthus amboinicus*.

Pharmaceutical Compositions

The present invention provides a pharmaceutical composition comprising a therapeutically effective amount of *Plectranthus amboinicus* crude extract and/or extract prepared by the separation process of the present invention. Another embodiment of the present invention provides a pharmaceutical composition comprising a therapeutically effective amount of *Plectranthus amboinicus* crude extract and/or extract prepared by the separation process of the present invention in combination with a therapeutically effective amount of *Centella asiatica* Urban extract.

The pharmaceutical composition of the present invention can be applied topically to the wounds, and it may be formulated as spray or non-spray. A spray form includes spray or solution; a non-spray form may be semi-solid or solid, preferably a solid form having a kinematic viscosity greater than water. Suitable formulations include but are not limited to suspensions, emulsions, creams, ointments, liniments and the like. If necessary, it may be sterilized or mixed with any pharmaceutically acceptable carriers, such as stabilizers, wetting agents and the like. Preferably, the pharmaceutical composition of the invention is formulated as ointments, wherein the preferred pharmaceutically acceptable carriers include but are not limited to higher fatty acids, waxes, lipids, glycerol, higher alcohols or synthetic lipids. The pharmaceutical composition of the present invention, no matter which form it is formulated in, may further comprise emollients, fragrances or colorings to increase the acceptability for various uses.

The therapeutically effective amounts of the *Plectranthus amboinicus* crude extract and/or extract and the *Centella asiatica* Urban extract are disclosed in U.S. Ser. No. 11/605,178, U.S. Pat. No. 4,318,906, CN 1353972A, U.S. Pat. Nos. 6,475, 536, 6,267,996, CN 1313124A, CN 93110425.4 and CN 1089497A, whereby the disclosures of the application are incorporated herein by reference in it entirety.

The pharmaceutical compositions of the present invention may be prepared by persons of ordinary skill in the art using conventional methods. One embodiment of the present invention includes a method for preparing an ointment comprising the following steps:
heating a ointment base in a water bath at about 50° C. until softened;
adding the softened ointment base in turn into a beaker containing the frozen dried *Plectranthus amboinicus* crude extract and/or extract;
adjusting the amount of the ointment base and the *Plectranthus amboinicus* crude extract and/or extract to make a *Plectranthus amboinicus* crude extract and/or extract ointment; and
storing the ointment at 4° C. in a refrigerator.

The content of the *Plectranthus amboinicus* crude extract is about 1% to 15% by weight of the ointment. The content of the *Plectranthus amboinicus* extract is about 0.1% to 5% by weight of the ointment.

Another embodiment of the present invention includes a method for preparing an ointment comprising the following steps:
heating a ointment base in a water bath at about 50° C. until softened;
adding the softened ointment base in turn into a beaker containing the frozen dried *Plectranthus amboinicus* crude extracts and/or extract to make a *Plectranthus amboinicus* crude extract and/or extract ointment;

homogenously mixing the *Plectranthus amboinicus* crude extract and/or extract ointment and the *Centella asiatica* Urban extract to make a *Centella asiatica* Urban extract+*Plectranthus amboinicus* crude extract and/or extract ointment; and storing the ointment at 4° C. in a refrigerator.

The content of the *Plectranthus amboinicus* crude extract is about 0.5% to about 5% by weight of the ointment and that of the *Centella asiatica* Urban extract is about 0.1% to about 20% by weight of the ointment. The content of the *Plectranthus amboinicus* extract is about 0.05% to about 2% by weight of the ointment and that of the *Centella asiatica* Urban extract is about 0.1% to about 20% by weight of the ointment. The weight ratio between the *Plectranthus amboinicus* crude extract and the *Centella asiatica* Urban extract is about 1:40 to about 1:4. The weight ratio between the *Plectranthus amboinicus* extract and the *Centella asiatica* Urban extract is about 1:60 to about 1:4.

According to the present invention, the ointment containing the fourth *Plectranthus amboinicus* extract (PA-W4) prepared by the stirring separation method of the invention and that containing PA-W4 in combination with the *Centella asiatica* Urban extract show a greater efficacy in enhancing healing of wounds than the ointment comprising the *Centella asiatica* Urban extract alone, the ointment comprising the *Plectranthus amboinicus* extracts prepared by the traditional column chromatographic separation method in combination with the *Centella asiatica* Urban extract, or other conventional drugs for enhancing wound healing (shown in the examples below). The amounts of the forth *Plectranthus amboinicus* extract and the *Centella asiatica* Urban extract in the ointment are about at least 0.01% and about at least 0.1% by weight, respectively. Preferably, the amount of the fourth *Plectranthus amboinicus* extract is about 0.01% to about 5%, more preferably about 0.1% to about 1%, most preferably about 0.25% to about 1%, by weight of the ointment. The amount of the *Centella asiatica* Urban extract is about 0.1% to about 20%, more preferably about 0.5% to about 9%, most preferably about 1% to about 3%, by weight of the ointment. Preferably, the weight ratio between the fourth *Plectranthus amboinicus* extract and the *Centella asiatica* extract is about 1:60 to about 1:4.

Utilities

The pharmaceutical compositions of the present invention can be used for treating disorders including but not limited to wounds and sores. In one preferred embodiment, said disorders are general trauma and bedsores, more preferably a diabetic patient's wound.

Persons skilled in the art should have no difficulty choosing the suitable routes and the dosages for treatments. According to the present invention, the preferred route is topical administration. Dosage will depend on the nature and condition of the disorder, age and health condition of the patient, administration route and any previous treatment. Persons skilled in the art should know that dosage may vary depending on the individual's age, size, health condition and other related factors.

The pharmaceutical compositions of the present invention may be conveniently used for manufacturing a wound dressing comprising a therapeutically effective amount of the *Plectranthus amboinicus* crude extract and/or extract and optionally a therapeutically effective amount of the *Centella asiatica* Urban extract, wherein said wound dressing includes but is not limited to bandage with adhesive, plaster patch and the like.

The following examples are provided to aid those skilled in the art in practicing the present invention. Even so, the examples should not be construed to unduly limit the present invention as modifications to and variations on the embodiments discussed herein may be made by those having ordinary skill in the art without departing from the spirit or scope of the present inventive discovery.

EXAMPLES

Materials

A. Ointment Base

The ointment base (BETAMETHASONE ointment base) used in the examples is purchased from Sinphar, Taiwan. The ointment base is used for preparing the ointments comprising *Centella asiatica* Urban extract and/or *Plectranthus amboinicus* extracts as well as the placebo in the biological assays.

B. CGS-21680

CGS-21680 (Sigma, batch number 093K4615) is a drug under clinical trials for healing wounds. 5 mg of CGS-21680 were added into 500 ml distilled water to prepare a 10 μg/ml CGS-21680 solution. The CGS-21680 solution was used as a comparative drug in the examples.

C. Regranex

Regranex 0.01% gel contains becaplermin, a recombinant human platelet-derived growth factor (fh-PDGF-BB), at a concentration of 100 μg/g (0.01%). It is a FDA-approved prescription drug for the treatment of deep neuropathic diabetic foot ulcers. Regranex was used as a comparative drug in the examples.

D. The *Centella asiatica* Urban Extract and the Ointment Comprising the Same

The method for preparing the *Centella asiatica* Urban extracts and the active component in the pharmaceutical composition of the present invention are well known to persons of ordinary skill in the art of herbal medicine extraction. The preferred method comprises:

extracting *Centella asiatica* by ethanol reflux extraction for 2 hours, and repeating it 2 to 3 times;

condensing the ethanol extract fluids to obtain the extracts;

retrieving the ethanol extracts, mixing and dissolving the extracts in water;

extracting with petroleum ether, chloroform, ethyl acetate separately, and then extracting with water-saturated n-butanol;

retrieving the solvent of n-butanol extracts under reduced pressure to obtain a cream-like substance and dissolving the substance in a small amount of methanol;

adding anhydrous acetone, several-fold, to the solution, to precipitate a yellowish crude total glucoside, drying and weighting the sediments;

adding a small amount of methanol to dissolve the crude total glucoside, mixing properly with silica gel and drying the mixture;

wet column packing with silica gel for chromatography and loading the sample silica gel;

eluting with chloroform, methanol and water (16:6:1 homogenous mixture) and collecting 18 components in turn; each component is 50 ml and the components are thin-layer spotting to compare with known controls;

combining components 9 to 15, concentrating, and then purifying with column using chloroform, methanol and water (14:6:1 homogenous mixture) for elution; and concentrating the same components and crystallizing with methanol repeatedly to obtain the white aciculate crystalline asiaticoside.

Furthermore, the drug substance of *Centella asiatica* Urban extracts containing asiaticoside and madecassic acid, with a purity greater than 70%, is available on the market. The commercial product CENTELLA ASIATICA PURIFIED EXTRACT can be purchased from NuLiv Science, Inc., Taiwan.

1% *Centella asiatica* Urban extract (S1) ointment was prepared as follows:

heating the ointment base in a water bath at about 50° C. until softened;

mixing 99 g of the softened ointment base with 1 g of *Centella asiatica* Urban extract (S1);

storing the ointment at 4° C. in a refrigerator.

The 1% S1 ointment was used in the examples as a comparative drug.

E. The *Plectranthus amboinicus* Extracts

The *Plectranthus amboinicus* extracts used in the biological assays were prepared by the preparation process of the present invention (the stirring separation method) and a column chromatographic separation method. The details of the preparation are described in the following preparation examples.

Example 1

Preparation of *Plectranthus amboinicus* Extracts by Stirring Separation Method 800 g of dried *Plectranthus amboinicus* leaves was dipped in a 95% alcohol having a volume ten-fold to the total weight of the dried leaves for 72 hours, and then the leaf extract was filtrated. The extraction procedure was repeated. The two leaf extracts were mixed to obtain a *Plectranthus amboinicus* crude extract and the crude extract was concentrated by a pressure-reducing rotary evaporator (Heidolph LABOROTA 4000, Eleya N-N series) to reduce the volume of the crude extract to about 5% of the original volume (i.e., to about one-half of the original weight of dried leaves).

The *Plectranthus amboinicus* crude extract was diluted with a high-polarity solvent to a volume ten-fold to the original one. The diluted *Plectranthus amboinicus* crudeextract was added into a bucket-like container containing DIAION® HP20 resin which was pre-treated by using methanol. The resin and the extract in the container were stirred at a speed of 3 to 10 rpm overnight. The fluid was then poured from the container. Double distilled water having a volume five-fold to the total weight of the dry leaves was added to the container. The resin was dipped in the water by stirring once in a while for one hour and the fluid was collected. The collected fluid (PA-W1) was concentrated and dried to obtain 2.4 g of dried product with a yield of 0.3%.

A sub-high-polarity solvent having a volume five-fold to the total weight of the dry leaves was further added to the container with the resin. The resin was dipped in the solvent by stirring once in a while for one hour and the fluid was collected. The process was repeated twice. The extracted fluids were mixed (PA-W2) and then concentrated and dried to obtain 4 g of dried product with a yield of 0.5%.

A medium-polarity solvent having a volume five-fold to the total weight of the dry leaves was further added to the container with the resin. The resin was dipped in the solvent by stirring once in a while for one hour and the fluid was collected. The process was repeated twice. The extracted fluids were mixed (PA-W3) and then concentrated and dried to obtain 6 g of dried product with a yield of 0.75%.

A low-polarity solvent having a volume five-fold to the total weight of the dry leaves was further added to the container with the resin. The resin was dipped in the solvent by stirring once in a while for one hour and the fluid was collected. The process was repeated three times. The extracted fluids were mixed (PA-W4) and then concentrated and dried to obtain 7.52 g of dried product with a yield of 0.94%.

Example 2

Preparation of *Plectranthus amboinicus* Extracts by Column Chromatographic Separation Method DIAION resin having a weight identical to that of the dried *Plectranthus amboinicus* leaves was dipped in methanol and packed into a chromatographic column. The packed DIAION resin was then washed with methanol having a volume one- to two-fold to the total weight of the DIAION resin, and subsequently washed with double distilled water having a volume five- to six-fold to the total weight of the DIAION resin.

800 g of dried *Plectranthus amboinicus* leaves was dipped in 95% alcohol having a volume ten-fold to the total weight of the dried leaves for 24 hours. After filtration, the leaves were further dipped in 95% alcohol having a volume ten-fold to the total weight of the dried leaves for 24 hours. The *Plectranthus amboinicus* extract fluids were mixed and concentrated by a pressure-reducing rotary evaporator to reduce the volume to about 2-3% of the original volume.

The extract obtained from the preceding steps was diluted with distilled water and loaded into the DIAION resin column. The column was eluted with a high-polarity solvent having a volume ten-fold to the total weight of the dried leaves. An eluted fraction (PA-C1) was collected and the yield was 0.38%.

The column was then eluted with a sub-high-polarity solvent having a volume five- to ten-fold to the total weight of the dried leaves. An eluted fraction (PA-C2) was collected and the yield was 0.5%.

The column was eluted again with a medium-polarity solvent having a volume five- to ten-fold to the total weight of the dried leaves. An eluted fraction (PA-C3) was collected and the yield was 0.78%.

Finally, the column was eluted with a low-polarity solvent having a volume five- to ten-fold to the total weight of the dried leaves. An eluted fraction (PA-C4) was collected and the yield was 0.67%.

Example 3

Composition Analysis of the *Plectranthus amboinicus* Extracts

Instruments and Equipments

High Performance Liquid Chromatography (HPLC) Spectra System, Thermo

Pump: Spectra-Physics P4000

Detector: UV/VIS Spectra-PhysicsSpectraSystem UV6000LP

Auto sampler: Thermo Separation Products AS3500

Software: Thermo Separation Products ChromQuest

System Controller: Thermo Separation Products SN4000

Conditions for Liquid Phase HPLC

Chromatographic column: Phenomenex, 4.6×250 nm, Luna 5μ silica (2)

Flow rate: 1.0 ml/min Pressure Limit: 250 kgf/cm$^2$

Sample amount: 10 μl

PDA conditions: Sampling period: 0.64 sec
  Wavelength range: 190-370 nm
  Channels: 270, 320 nm
Elution Profile:

|             | Time (min) | | | |
| --- | --- | --- | --- | --- |
| Mobile phase | 0 | 15 | 45 | 50 |
| n-hexane | 95% | 85% | 30% | 95% |
| Ethyl acetate | 5% | 15% | 70% | 5% |

Figure 2:
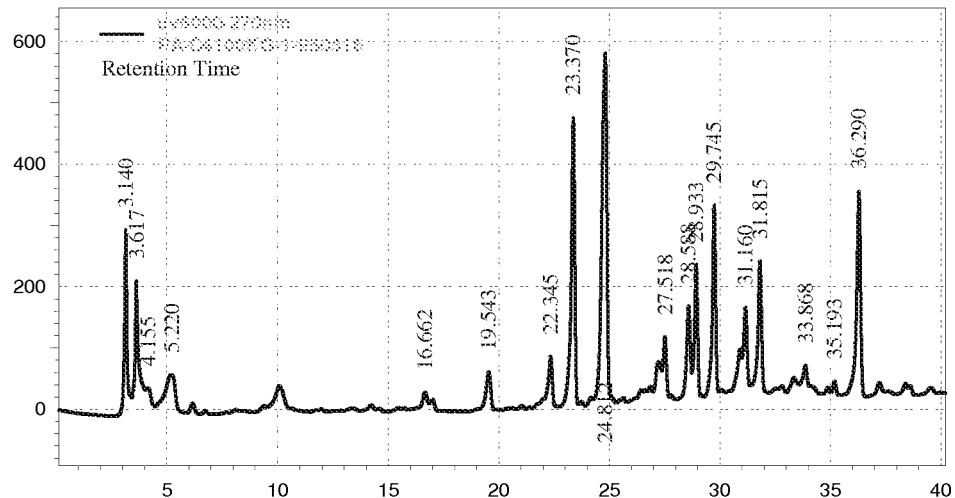
FIG. 2 shows the chromatographic spectrum of the *Plectranthus amboinicus* extract (PA-C4) prepared by column chromatographic separation. The spectrum was determined by Reverse Phase HPLC at UV 270 nm.

The chromatographic spectrum of the PA-W4 extract obtained by stirring separation and that of the PA-C4 extract obtained by column chromatographic separation are shown in FIGS. 1 and 2, respectively. The PA-W4 has HPLC peaks at the following retention time:

| Peak | Retention time (min) |
| --- | --- |
| 1 | 5.5 |
| 2 | 9.6 |
| 3 | 20.0 |
| 4 | 22.5 |
| 5 | 23.5 |
| 6 | 24.8 |
| 7 | 27.7 |
| 8 | 27.8 |
| 9 | 28.6 |
| 10 | 28.9 |
| 11 | 29.7 |
| 12 | 31.0 |
| 13 | 31.9 |
| 14 | 36.6 |
| 15 | 37.8 |

Example 4

Preparation of Ointments Comprising *Plectranthus amboinicus* Extracts and Ointments Comprising *Centella asiatica* Urban Extract (S1) and *Plectranthus amboinicus* Extracts Suitable amounts of ointment base, PA-W4 extract and PA-C4 extract were measured. The ointment base was preheated in a water bath at about 50° C. until softened and added into beakers containing the PA-W4 extract and the PA-C4 extract to obtain a 0.25% PA-W4 ointments and a 0.25% PA-C4 ointment. The weight ratio of the ointment base to the *Plectranthus amboinicus* extracts was 99.75:0.25. The obtained ointments were then mixed with *Centella asiatica* Urban extract (S1) in a weight ratio of 99:1 to obtain a DCR-WH1-W ointment (1% S1+0.25% PA-W4) and a DCR-WH1-C ointment (1% S1+0.25% PA-C4).

Biological Assays

Example 5

Animal Experiments for Wound Closures in Diabetic Rats

[Animal Experiments]
Induction of High Blood Sugar in the Animals
  Rats with a body weight of over 300 g were administered with Streptozotocin (STZ, 65 mg/kg, i.p.) to induce high blood sugar. Rats with successfully induced high blood sugar (over 300 mg/DL) were selected to conduct the wound closure tests two months after high-blood-sugar syndromes appeared.

Trauma Surgeries for the Diabetic Animals
  i. The high-blood-sugar animals with a body weight of lower than 300 g were eliminated and the rest were randomized into 6 groups.
  ii. The animals were anesthetized with pentobarbital and the hair on the surgical area (dorsal area) was removed. The surgical areas and instruments were then sterilized with 75% alcohol before operation.
  iii. The skins on the dorsal medium areas (4, 6 and 8 cm from the midpoint of two scapula) were excised (full thickness) using a round cutting blade with a diameter of 1 cm.

Measuring the Wounds, Applying Testing Materials, and Preventing the Wounds from Being Scratched
  i. A standard ruler was placed beside the wounds and pictures were taken.
  ii. A thin layer of the test materials formulated as ointments and 0.05 ml of CGS21680 solution were applied to each wound.
  iii. The wounds were covered with gauze and hoods were worn on the rats' necks.

Test materials were applied to the rats twice a day (morning and evening) and the wounds were measured at each time point.

After the experiments were finished, the regenerated skins were taken for biochemistry and histology analysis.

[Wound Area Analysis]
  A standard ruler was placed beside the wounds when pictures were taken. The length of the wounds was standardized according to the scale of the standard ruler in the pictures before the wounds were analyzed with the image processing software Image-Pro (Media Cybernetics, Inc.) to avoid the errors caused by different picturing distances.

[Data Analysis and Statistics]
  The areas of the three wounds on the rats' backs were analyzed by Image-Pro. The wound areas of day zero were the original wound areas. The original wound areas minus the wound areas at different time points were divided by the original wound areas to get the wound closure percentages. The mean of the three wound closure percentages of each rat represents the wound closure of each rat. Four to seven rats per group were used for each test materials. The data was shown as mean±standard error (SEM). The p-values of the test results were calculated by t-test in statistics software sigma statis (Systat software Inc.). $P<0.05$ means there is a significant difference, and it is marked with * on the statistics charts or tables. $P<0.01$ means there is a very significant difference, and it is marked with  on the statistics charts or tables. $P<0.001$ means there is an extremely significant difference, and it is marked with * on the statistics charts or tables.

Example 6

Figure 3:
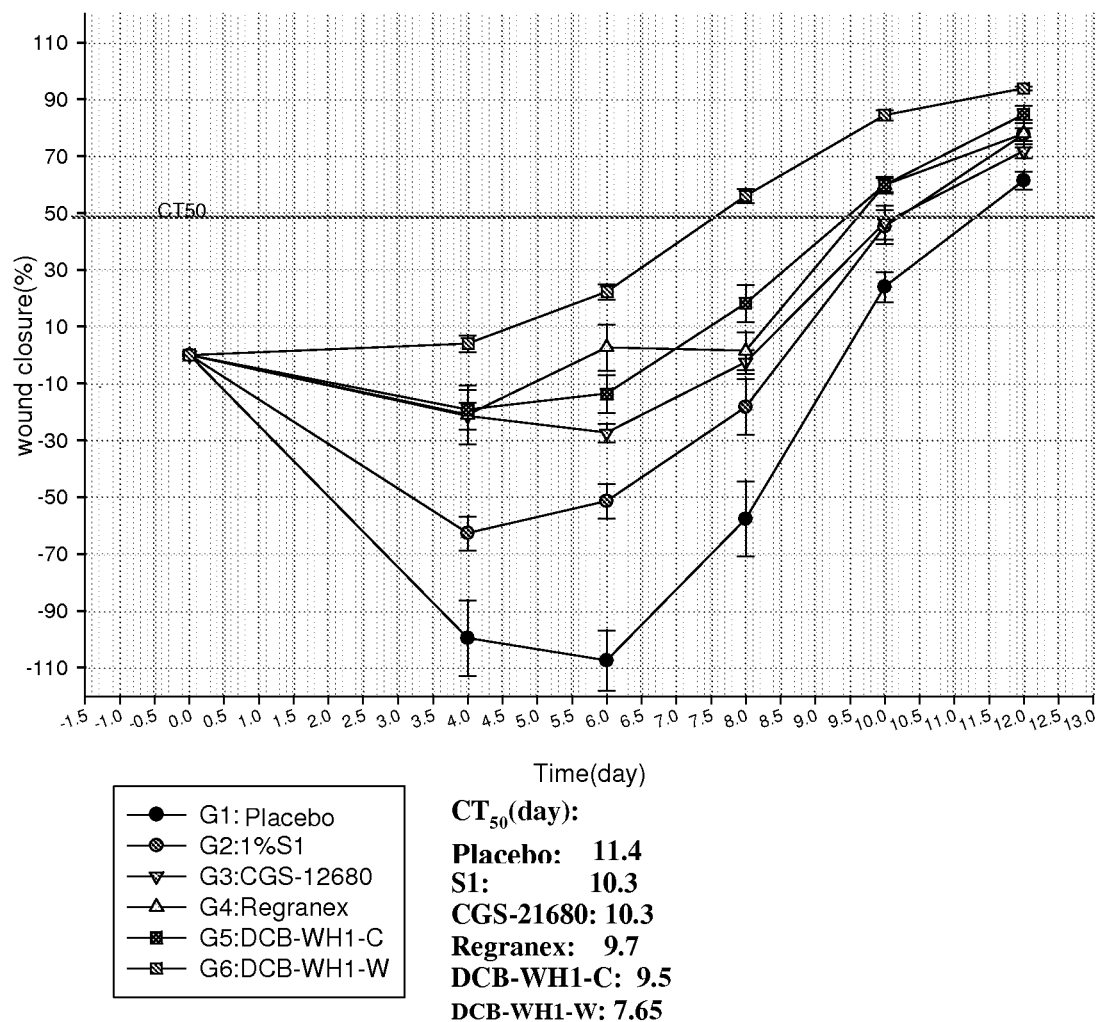
FIG. 3 shows wound closures in STZ-induced diabetic rats. Group 1: wound applied with placebo (ointment without medicament); Group 2: wound applied with ointment containing 1% *Centella asiatica* Urban extracts (S1); Group 3: wound applied with CGS-21680 (10 µg/ml); Group 4: wound applied with Regranex; Group 5: wound applied with DCB-WH1-C (ointment comprising 1% S1 and 0.25% PA-C4); Group 6: wound applied with DCB-WH1-W (ointment comprising 1% S1 and 0.25% PA-W4).

Comparison of the Efficacies of 1% S1, CGS-21680, Regranex, DCB-WH1-C and DCB-WH1-W on Wound Closures in STZ-Induced Diabetic Rats The purpose of this example is to compare the efficacy of the composition of the present invention and that of the commercially available products on wound closures. The wound closure animal experiments were conducted according to Example 5. On day 0, 4, 6, 8, 10 and 12 after the treatments of placebo (Group 1), 1% S1 ointment (Group 2), CGS-21680 (Group 3), Regranex (Group 4), DCB-WH1-C (Group 5) and DCB-WH1-W (Group 6), the wound areas of all experimental groups were measured and the wound closure percentages and $CT_{50}$ (time required for 50% wound closure) values were calculated. The results are shown in FIG. 3 and Table 1. The P-values of the paired comparison of wound closure percentages of the experimental groups are shown in Table 2.

TABLE 1

Wound closure percentages and $CT_{50}$ of the experimental groups treated with placebo, 1% S1 ointment, CGS21680, Regranex, DCB-WH1-C and DCB-WH1-W

| | | Wound closure percentage (%) | | | | | $CT_{50}$ |
|---|---|---|---|---|---|---|---|
| Groups | Test materials | Day 4 | Day 6 | Day 8 | Day 10 | DAY 12 | (day) |
| 1 | Placebo | −99.6 ± 13.3 | −107.6 ± 10.5 | −45.14 ± 13 | 19.9 ± 5.3 | 61.5 ± 3.1 | 11.4 |
| 2 | 1% S1 | −62.7 ± 6.0 | −51.4 ± 6.0 | −18.2 ± 9.7 | 45.2 ± 5.9 | 77.7 ± 2.3 | 10.3 |
| 3 | CGS-2168 | −21.3 ± 4.8 | −27.38 ± 3.2 | −2.4 ± 4.1 | 46.7 ± 6.0 | 71.7 ± 2.4 | 10.3 |
| 4 | Regranex | −21.0 ± 10.4 | 2.7 ± 8.1 | 1.46 ± 6.7 | 59.9 ± 2.6 | 78.0 ± 4.8 | 9.7 |
| 5 | DCB-WH1-C | −19.2 ± 7.0 | −13.6 ± 6.7 | 18.3 ± 6.6 | 59.9 ± 2.9 | 84.8 ± 3.0 | 9.5 |
| 6 | DCB-WH1-W | 4.1 ± 2.9 | 22.3 ± 2.7 | 56.0 ± 2.5 | 84.5 ± 1.8 | 93.9 ± 0.7 | 7.65 |

TABLE 2

The P-values of the paired comparison of wound closure percentages of the experimental groups

| Day | Group vs Group | | P-values | |
|---|---|---|---|---|
| 4 | 2 | 3 | 0.000289 | *** |
| 4 | 2 | 4 | 0.0054565 | ** |
| 4 | 2 | 5 | 0.0004544 | *** |
| 4 | 2 | 6 | 0.000001203 | *** |
| 4 | 3 | 4 | 0.9788 | |
| 4 | 3 | 5 | 0.5697 | |
| 4 | 3 | 6 | 0.00075098 | *** |
| 4 | 4 | 5 | 0.7119 | |
| 4 | 4 | 6 | 0.0276 | * |
| 4 | 5 | 6 | 0.0157 | * |
| 6 | 2 | 3 | 0.0055961 | ** |
| 6 | 2 | 4 | 0.00039598 | *** |
| 6 | 2 | 5 | 0.001875 | ** |
| 6 | 2 | 6 | 0.0000005765 | *** |
| 6 | 3 | 4 | 0.0049146 | ** |
| 6 | 3 | 5 | 0.0947 | |
| 6 | 3 | 6 | 0.000000339 | *** |
| 6 | 4 | 5 | 0.1504 | |
| 6 | 4 | 6 | 0.0356 | * |
| 6 | 5 | 6 | 0.0005663 | *** |
| 8 | 2 | 3 | 0.1659 | |
| 8 | 2 | 4 | 0.1454 | |
| 8 | 2 | 5 | 0.0113 | * |
| 8 | 2 | 6 | 0.000023634 | *** |
| 8 | 3 | 4 | 0.62 | |
| 8 | 3 | 5 | 0.0238 | * |
| 8 | 3 | 6 | 0.0000002486 | *** |
| 8 | 4 | 5 | 0.1087 | |
| 8 | 4 | 6 | 0.000016991 | *** |
| 8 | 5 | 6 | 0.00031843 | *** |
| 10 | 2 | 3 | 0.8675 | |
| 10 | 2 | 4 | 0.0954 | |
| 10 | 2 | 5 | 0.0509 | |
| 10 | 2 | 6 | 0.000084357 | *** |
| 10 | 3 | 4 | 0.1274 | |
| 10 | 3 | 5 | 0.0740 | |
| 10 | 3 | 6 | 0.00011665 | *** |
| 10 | 4 | 5 | 0.9934 | |
| 10 | 4 | 6 | 0.000055221 | *** |
| 10 | 5 | 6 | 0.000026694 | *** |

On day 4, the wound closure percentages of Groups 3, 4, 5 or 6 are significantly higher than those of Groups 1 and 2 (P<0.01), and the wound closure percentage of Group 6 is even significantly higher than those of Groups 3, 4 and 5 (P<0.05). On day 6, the wound closure percentages of Groups 3, 4, 5 and 6 are significantly higher than those of Groups 1 and 2 (P<0.01 and P<0.001, respectively), and the wound closure percentage of Group 6 is even significantly higher than those of Group 3, 4 or 5 (P<0.05 or P<0.001). On day 8, the wound closure percentages of Groups 5 and 6 are significantly higher than those of Groups 2 (P<0.05), and the wound closure percentage of Group 6 is even significantly higher than those of Groups 3, 4 and 5 (P<0.001). On day 10, the wound closure percentage of Group 6 is significantly higher than those of other groups (P<0.001). The $CT_{50}$ for Groups 1 to 6 are 11.4, 10.3, 10.36, 9.4, 9.5 and 7.65 days, respectively.

In summary, the DCB-WH1-W ointment of the present invention has a superior efficacy over other test materials, i.e., ointment base, 1% S1 ointment, CGS21680, Regranex and DCB-WH1-C.

Example 7

Figure 4:
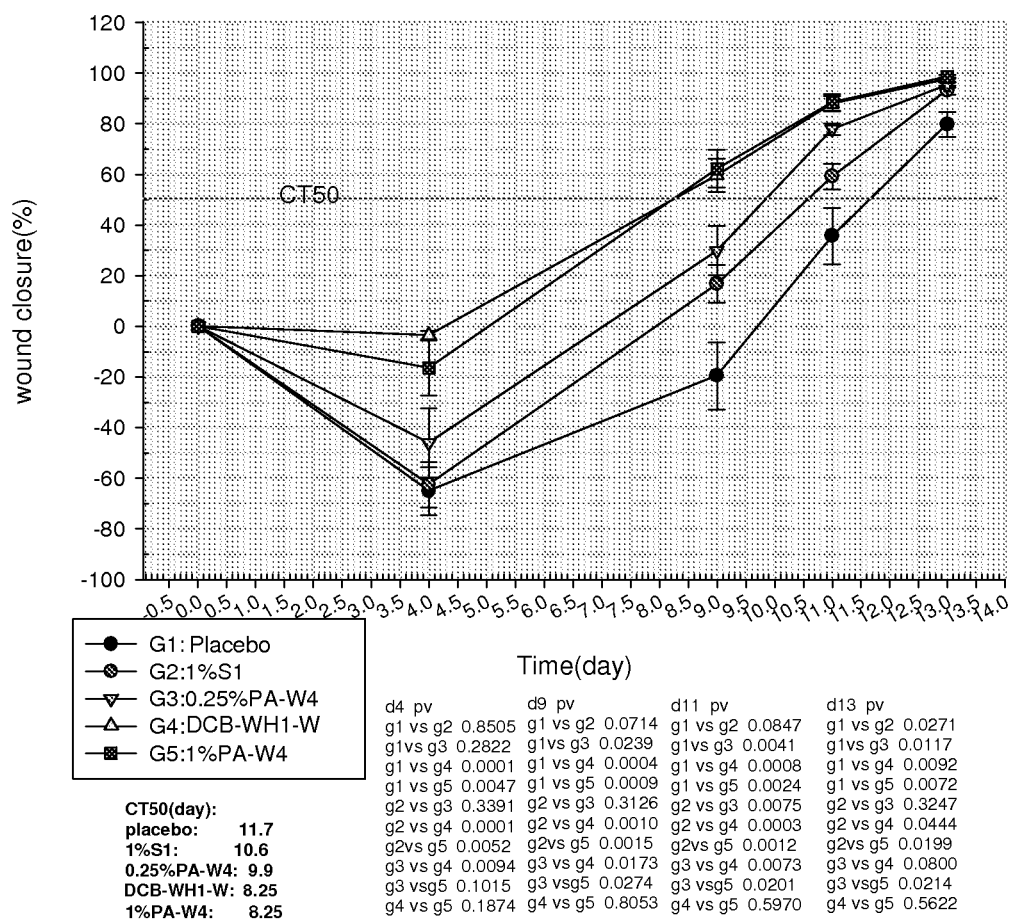
FIG. 4 shows wound closures in STZ-induced diabetic rats. Group 1: wound applied with placebo (ointment without medicament); Group 2: wound applied with ointment containing 1% *Centella asiatica* Urban extracts (S1); Group 3: wound applied with ointment containing 0.25% PA-W4; Group 4: wound applied with DCB-WH1-W (ointment comprising 1% S1 and 0.25% PA-W4); Group 5: wound applied with ointment containing 1% PA-W4.

Comparison of the Efficacies of 1% S1, 0.25% PA-W4, DCB-WH1-W and 1% PA-W4 on Wound Closures in STZ-Induced Diabetic Rats The purpose of this example is to compare the efficacy of DCB-WH1-W with that of its active ingredients in wound closures. The test materials are placebo (Group 1), 1% S1 ointment (Group 2), 0.25% PA-W4 ointment (Group 3), DCB-WH1-W (Group 4) and 1% PA-W4 ointment (Group 5). The wound closure animal experiments were conducted according to Example 5. On day 0, 4, 9, 11 and 13 after the treatment with the test materials, the wound areas of all experimental groups were measured and the wound closure percentages and $CT_{50}$ were calculated. The results are shown in FIG. 4 and Table 3. The P-values of the paired comparison of wound closure percentages of the experimental groups are shown in Table 4.

TABLE 3

Wound closure percentages and $CT_{50}$ of the experimental groups treated with placebo, 1% S1 ointment, 0.25% PA-W4 ointment, DCB-WH1-W and 1% PA-W4 ointment

| | | Wound closure percentage (%) | | | | $CT_{50}$ |
|---|---|---|---|---|---|---|
| Groups | Test materials | Day 4 | Day 9 | Day 11 | Day 13 | (day) |
| 1 | Placebo | −65.07 ± 9.5 | −19.6 ± 13.4 | 35.7 ± 11.1 | 79.8 ± 4.9 | 11.7 |
| 2 | 1% S1 | −62.55 ± 8.9 | 16.8 ± 7.5 | 59.1 ± 5.1 | 93.2 ± 1.7 | 10.6 |
| 3 | 0.25% PA-W4 | −46.1 ± 13.8 | 29.9 ± 9.8 | 77.9 ± 2.3 | 95.2 ± 1.0 | 9.9 |

TABLE 3-continued

Wound closure percentages and $CT_{50}$ of the experimental groups treated with placebo, 1% S1 ointment, 0.25% PA-W4 ointment, DCB-WH1-W and 1% PA-W4 ointment

| Groups | Test materials | Wound closure percentage (%) | | | | $CT_{50}$ (day) |
|---|---|---|---|---|---|---|
| | | Day 4 | Day 9 | Day 11 | Day 13 | |
| 4 | DCB-WH1-W | −3.51 ± 1.7 | 59.7 ± 6.6 | 87.9 ± 3.1 | 97.42 ± 1.0 | 8.25 |
| 5 | 1% PA-W4 | −16.5 ± 10.9 | 62.2 ± 7.4 | 88.45 ± 3.3 | 98.59 ± 0.8 | 8.25 |

TABLE 4

The P-values of the paired comparison of wound closure percentages of the experimental groups

| Day | Group vs Group | | P-values | |
|---|---|---|---|---|
| 4 | 1 | 2 | 0.8505 | |
| 4 | 1 | 3 | 0.2822 | |
| 4 | 1 | 4 | 0.0001 | *** |
| 4 | 1 | 5 | 0.0047 | ** |
| 4 | 2 | 3 | 0.3391 | |
| 4 | 2 | 4 | 0.0001 | *** |
| 4 | 2 | 5 | 0.0052 | ** |
| 4 | 3 | 4 | 0.0094 | ** |
| 4 | 3 | 5 | 0.1015 | |
| 4 | 4 | 5 | 0.1874 | |
| 9 | 1 | 2 | 0.0714 | |
| 9 | 1 | 3 | 0.0239 | * |
| 9 | 1 | 4 | 0.0004 | *** |
| 9 | 1 | 5 | 0.0009 | *** |
| 9 | 2 | 3 | 0.3126 | |
| 9 | 2 | 4 | 0.0010 | ** |
| 9 | 2 | 5 | 0.0015 | ** |
| 9 | 3 | 4 | 0.0173 | * |
| 9 | 3 | 5 | 0.0274 | * |
| 9 | 4 | 5 | 0.8053 | |
| 11 | 1 | 2 | 0.0847 | |
| 11 | 1 | 3 | 0.0041 | ** |
| 11 | 1 | 4 | 0.0008 | *** |
| 11 | 1 | 5 | 0.0024 | ** |
| 11 | 2 | 3 | 0.0075 | ** |
| 11 | 2 | 4 | 0.0003 | *** |
| 11 | 2 | 5 | 0.0012 | ** |
| 11 | 3 | 4 | 0.0073 | ** |
| 11 | 3 | 5 | 0.0201 | * |
| 11 | 4 | 5 | 0.5970 | |
| 13 | 1 | 2 | 0.0271 | * |
| 13 | 1 | 3 | 0.0117 | * |
| 13 | 1 | 4 | 0.0092 | ** |
| 13 | 1 | 5 | 0.0072 | ** |
| 13 | 2 | 3 | 0.3247 | |
| 13 | 2 | 4 | 0.0444 | * |
| 13 | 2 | 5 | 0.0199 | * |
| 13 | 3 | 4 | 0.0800 | |
| 13 | 3 | 5 | 0.0214 | * |
| 13 | 4 | 5 | 0.5622 | |

On day 4, the wound closure percentages of Groups 4 or 5 are significantly higher than those of Groups 1 and 2 (P<0.01). On day 9, the wound closure percentages of Groups 4 and 5 are significantly higher than those of Group 1 (P<0.001), Group 2 (P<0.01) and Group 3 (P<0.05), and the wound closure percentage of Group 3 is also significantly higher than that of Group 1 (P<0.05). On day 11, the wound closure percentages of Groups 3, 4 and 5 are significantly higher than that of Group 2 (P<0.01), and the wound closure percentages of Groups 4 and 5 are significantly higher than that of Group 3 (P<0.05). On day 13, the wound closure percentage of Groups 4 and 5 are significantly higher than those of Group 1 (P<0.01) and Group 2 (P<0.05), and the wound closure percentage of Group 5 is significantly higher than that of Group 3 (P<0.05). There is no significant difference between Groups 4 and 5 on days 4, 9, 11 and 13. The $CT_{50}$ for Groups 1 to 5 are 11.7, 10.6, 9.9, 8.25 and 8.25 days, respectively.

In summary, the efficacy of the ointment comprising 1% PA-W4 (1% PA-W4 ointment) on wound closures is equivalent to that of the DCB-WH1-W (1% S1+0.25% PA-W4) ointment. The 1% PA-F4 and DCB-WH1-W ointments of the present invention have a superior efficacy over the ointment base, the 1% S1 ointment and the 0.25% PA-W4 ointment.

What is claimed is:

1. A method of treating wounds in a diabetic patient in need thereof comprising administering to said patient a pharmaceutical composition comprising a therapeutically effective amount of a *Plectranthus amboinicus* extract obtained by:
   a) contacting dried *Plectranthus amboinicus* leaves with 95% alcohol, filtering and repeating to provide two leaf extracts, wherein the two leaf extracts are mixed together to provide a *Plectranthus amboinicus* crude extract;
   b) concentrating the *Plectranthus amboinicus* crude extract;
   c) diluting the concentrated *Plectranthus amboinicus* crude extract with a high-polarity solvent to provide a diluted crude extract;
   d) adding the diluted crude extract to resin pre-treated with methanol, stirring and dipping in double distilled water to provide a first extract and resin; and further treating the spent resin to provide additional extracts by:
      i.) extracting the resin of (d) with a sub-high-polarity solvent and collecting a second extract;
      ii.) further extracting the resin of (i) with a medium-polarity solvent and collecting a third extract and spent resin; and
      iii.) further extracting the resin of (ii) with a low-polarity solvent and collecting a fourth extract; and
   e) obtaining the *Plectranthus amboinicus* extract, wherein the *Plectranthus amboinicus* extract contains one or more extracts selected from the first, second, third and fourth extracts; and wherein the composition optionally further comprises a pharmaceutically acceptable carrier, diluent or excipient.

2. The method of claim 1, wherein said composition further comprises a therapeutically effective amount of *Centella asiatica* Urban extract.

3. The method of claim 2, wherein the weight ratio of the *Plectranthus amboinicus* extract to the *Centella asiatica* extract is about 1:60 to about 1:4.

4. The method of claim 1, wherein said wound is bedsores.

5. The method of claim 2, wherein said wound is bedsores.

6. The method of claim 3, wherein said wound is bedsores.

* * * * *